Figure 1:
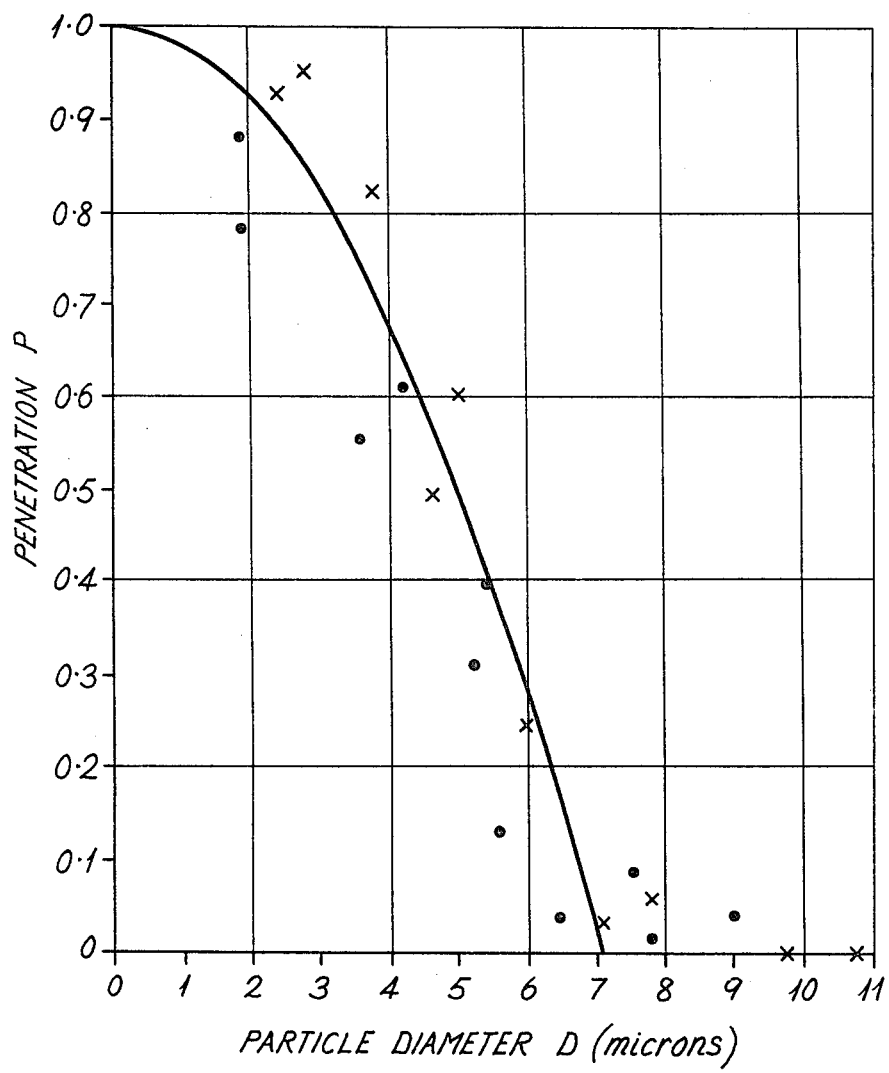

United States Patent [19]

Greenough et al.

[11] 4,350,507
[45] Sep. 21, 1982

[54] RESPIRABLE PARTICLE SAMPLING INSTRUMENTS

[75] Inventors: George K. Greenough; Richard C. Brown, both of Sheffield, England

[73] Assignee: National Research Development Corporation, London, England

[21] Appl. No.: 240,166

[22] Filed: Mar. 3, 1981

[30] Foreign Application Priority Data

Mar. 4, 1980 [GB] United Kingdom ............... 8007385

[51] Int. Cl.³ .......................................... B01D 50/00
[52] U.S. Cl. ...................................... 55/270; 55/372; 55/472; 55/473; 55/482; 55/487; 55/524; 55/528; 55/DIG. 24; 55/DIG. 35; 55/DIG. 42; 73/28; 73/863.23; 128/201.25
[58] Field of Search ................ 55/270, 524, 527, 528, 55/487, 482, 372, 467, DIG. 42, DIG. 13, DIG. 35, 318, 350, 472–473, DIG. 24; 73/28, 863.23; 128/201.25

[56] References Cited

U.S. PATENT DOCUMENTS

| | | | |
|---|---|---|---|
| 2,966,960 | 1/1961 | Rochlin | 55/DIG. 13 X |
| 3,102,014 | 8/1963 | Aitkenhead | 55/487 X |
| 3,149,942 | 9/1964 | Finch | 55/524 X |
| 3,171,820 | 3/1965 | Volz | 55/528 X |
| 3,657,992 | 4/1972 | Minnick, Jr. | 55/487 X |
| 3,672,126 | 6/1972 | Goettle | 55/467 X |
| 4,133,202 | 1/1979 | Marple | 55/270 X |
| 4,136,688 | 1/1979 | Gorman | 128/201.25 |
| 4,141,703 | 2/1979 | Mulchi | 55/527 X |
| 4,155,247 | 5/1979 | Kaczmarek et al. | 55/270 X |

FOREIGN PATENT DOCUMENTS

| | | |
|---|---|---|
| 1426432 | 2/1976 | United Kingdom . |
| 1454543 | 11/1976 | United Kingdom ................ 55/487 |
| 1495020 | 12/1977 | United Kingdom . |
| 463453 | 4/1975 | U.S.S.R. ...................... 128/201.25 |

OTHER PUBLICATIONS

Brink, Jr., J. A. and Porthouse, J. D., "Efficient Dust Control Via New Sampling Technique", *Chemical Engineering*, (Mar. 10, 1969), pp. 106–110.

Primary Examiner—Kathleen J. Prunner
Attorney, Agent, or Firm—Cushman, Darby & Cushman

[57] ABSTRACT

A respirable particle sampling instrument passes air with a fan through a passage having first a pre-filter thereacross to collect non-respirable airborne particles and then a main filter to collect respirable particles, the pre-filter being formed by a random fibrous network having interstices of such size and distribution as to capture a major proportion of the non-respirable particles within a prescribed range of velocity for which particle capture is predominantly by inertial impaction. The pre-filter suitably comprises porous foamed plastics material, preferably in a structure of contiguous layers having successively changing pore sizes and distribution, preferably of a polyester, and preferably having an oil coating. The pre-filter will normally have a penetration function approximating the so-called Johannesburg curve.

7 Claims, 9 Drawing Figures

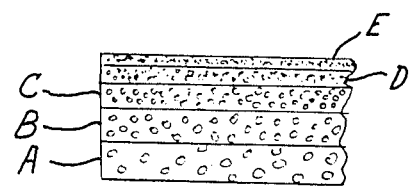
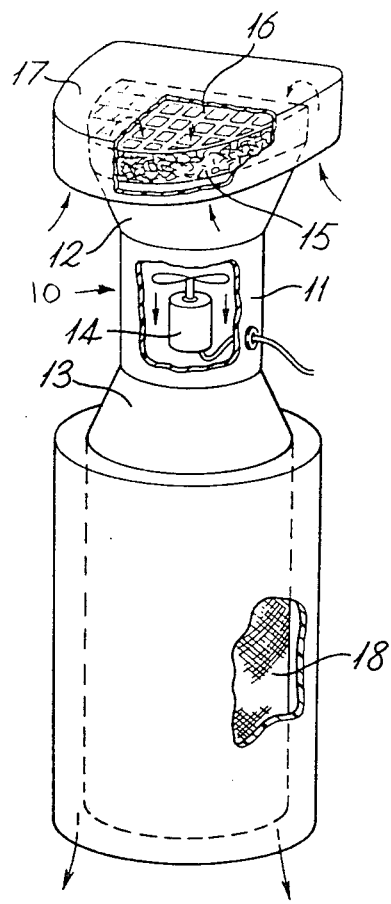
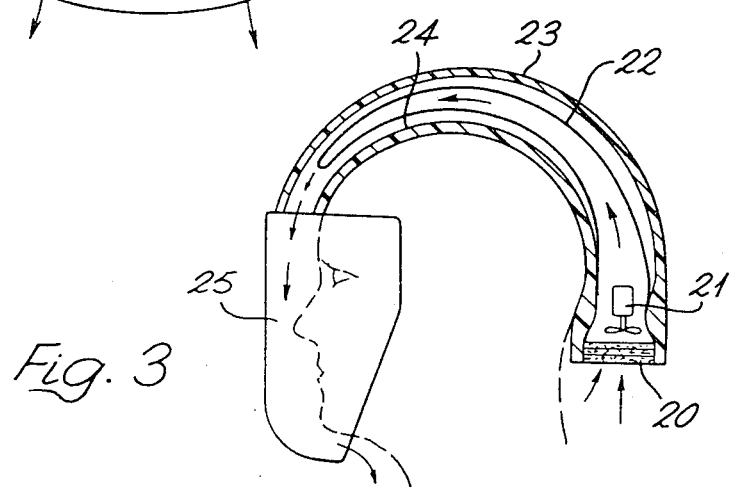

RESPIRABLE PARTICLE SAMPLING INSTRUMENTS

Airborne dust in a working environment may be inhaled by workers and cause respiratory impairment. It is accordingly appropriate in some circumstances to limit the concentration of airborne dust to a level which is considered tolerable: indeed this is a legal requirement in some industrial situations.

This, in turn, leads to a requirement to sample the air and measure the concentration of hazardous dust particles in order to assess whether a given environment is tolerable or not.

In circumstances where the dust concentration varies from point to point in the working environment, it may be necessary for sampling instruments to be carried or worn by the workers and such personal instruments, together with associated power supplies, must necessarily be small and lightweight to be acceptable. A widely used technique employed for such personal instruments is to draw air at a controlled rate through a piece of filter material of known weight and then to weigh the filter material after a measured period of time to determine from the increase in weight, the air flow rate, and period of use, the weight of airborne dust per unit volume of air. However, because of the limitations on size and weight such personal gravimetric sampling instruments can only operate at a small air flow rate, the weight of collected dust over a reasonable period of time is correspondingly small, and so precise weighing is required if suitably accurate results are to be obtained. These instruments accordingly require specialist attention and are costly to employ.

Similar considerations of size and weight can also apply to gravimetric sampling instruments for use at a fixed point if the instrument, with its power supply, has to be carried any relatively long distance to the sampling point, as can be the case in mining, or if use of a large instrument could impede working operations.

A further requirement for a dust sampling instrument in many instances is that the instrument should sample only dust particles that are small enough to reach the lungs in order to provide a more accurate measure of the respirable hazard. This requirement is commonly met by the use of one of two forms of particle size selector. One such form is a so-called parallel plate elutriator in which air flow to a sampling instrument is first passed between horizontal parallel plates having a length and spacing such that the larger, non-respirable particles of airborne dust have time to deposit therebetween rather than continue to the sampler. The other form of selector involves a cyclone in which air is caused to rotate and deposit non-respirable particles by centrifugal force.

The size of both of these forms of selector increases with the air flow rate capability thereof and so, again, is subject to limitation in many situations requiring dust sampling. A further disadvantage in the case of parallel plate elutriators is the inherent requirement to maintain the plates horizontal, and this renders such selectors unsuitable for incorporation in a personal dust sampling instrument.

An object of the present invention is to improve the above situation by providing a respirable particle sampling instrument operable at higher air flow rates, without suffering disadvantages of size and weight.

To this end the present invention provides a respirable particle sampling instrument comprising a housing defining an air passageway therethrough and having mounted therein an electric fan to draw and pass air into and through said passageway, a main filter across the passageway to collect respirable particles borne by such air, and a pre-filter located across the passageway upstream of the main filter to collect non-respirable particles borne by said air, said pre-filter being formed by a random fibrous network having interstices of such size and distribution as to capture a major proportion of the non-respirable airborne particles in an air flow therethrough within a prescribed range of velocity for which particle capture is predominantly by inertial impaction. In this connection it is to be understood that particle capture in a filter can involve both sedimentation and inertial impaction, but that the latter dominates at higher air flow velocities.

While the pre-filter can be formed by a mat of discrete fibres, it suitably comprises porous foam plastics material and in a presently preferred form comprises a structure of contiguous layers of such material having successively changing pore size and distribution therethrough from one layer to the next. Also, the foam material is preferably a polyester for consistency, and may be provided with an oil coating.

Also, the pre-filter can, and for most purposes will, have a penetration function which approximates the so-called Johannesburg curve (which defines a penetration function recommended by a pneumoconiosis conference in Johannesburg in 1959, and was reported in the conference proceedings by Orenstein, 1960).

The main filter is suitably of bag form and the fan of axial type, but alternatives are possible.

The proposed instrument can, of course, be employed for fixed site sampling, but it is particularly advantageous for personal mobile use. In the latter case the instrument can be beneficially incorporated in a helment according to U.K. Pat. No. 1,426,432 or 1,495,020 in which a bag filter and fan are already provided to supply the user with respiration air.

In order that the invention may be more fully understood and readily carried into effect, the same will now be described further by way of example and with reference to the accompanying drawings, in which:

FIG. 1 graphically illustrates the Johannesburg curve and related penetration characteristics respectively of a pre-filter according to the invention and a cyclone selector, FIG. 2 schematically illustrates one form of sampling instrument according to the invention, FIG. 3 similarly illustrates another such form of instrument, and FIG. 4 schematically illustrates a particular form of pre-filter.

FIGS. 5A–E are greatly enlarged illustrations of the random fibrous network and foam plastic material of the layers of the pre-filter of FIG. 4.

In FIG. 1 the solid line trace is the Johannesburg curve, which shows the penetration of unit density spheres through an idealised parallel plate elutriator as a function of the sphere diameter, penetration and diameter being represented respectively by the vertical axis P and the horizontal axis D. The penetration value of the function for any particle is euqal to that for a unit density sphere having the same settling velocity as the particle.

The related penetration characteristics represented by the crosses in FIG. 1 are those for a pre-filter according to the invention. This filter comprised a porous polyester foam filter having pore size of approximately 0.3 mm, 3200 pores per meter (ppm), and being 7 mm thick. The results of FIG. 1 were obtained by application to the filter at a velocity of 20 cm/s, of monodisperse aerosols of sucrose of between 2 and 11 micrometers diameter. These aerosols were produced by a vibrating orifice aerosol generator, made electrically neutral by a small radio-active source and detected by an optical particle counter. Initially, large particles were not captured efficiently-seemingly because of failure to adhere on contact. However, this was corrected by immersing the foam in a mixture of low vapour pressure oil and alcohol, and allowing the alcohol to evaporate and to leave a thin-film of oil on the fibres of the foam. It appears that porous foam materials more readily retain such a coating than do filters of discrete fibres. This is through to arise from the fact that creation of the porous foam interstices by multiple spherical expansions within the initial body of material produces fibres seen to be of generally triangular cross-section with concavely curved sides, and this concavity affords better retention than in a discrete fibre of circular or other wholly convex cross-section.

The related transfer characteristics represented by the dots in FIG. 1 are those for a cyclone selector and are shown for comparative purposes.

Clearly, from FIG. 1, a pre-filter of the presently proposed form can provide penetration characteristics which closely approximate to the Johannesburg curve and are comparable with those of existing, alternative selectors.

The foam filter referred to in connection with FIG. 1 was in fact an earlier form tested during development of the invention, and development has continued with the use of filters comprising contiguous layers of foam material having successively varying characteristics from one layer to the next. These multi-layer filters can give further improved results.

For example one such multi-layer filter comprised five successive layers of porous foam as above but with differing characteristics as follows: 12 mm thickness having 400 ppm, 12 mm of 800 ppm, 9 mm of 1200 ppm, 6 mm of 1800 ppm, and 4 mm of 3200 ppm. An area of 1250 mm$^2$ of this filter could collect 1.5 gm of a given dust before the collection characteristics changed by 10% i.e. the integrated weight of dust penetrating the filter becomes 10% less than it would be with a clean filter. This can be compared with the performance of a single layer foam filter of a thickness to give the same initial performance but collecting only about 0.25 gm of the dust before its collection characteristic suffered at 10% change.

The instrument of FIG. 2 comprises a generally tubular housing generally designated at 10 and which has an air passageway therethrough, the housing having a narrower intermediate portion 11 flaring outwardly at its opposite ends to diametrally enlarged end portions 12 and 13. The housing portion 11 carries a battery-operable axial fan 14 therein, the batteries being located in a compartment formed with the housing or in a separate compartment having a lead connection to the fan. A pre-filter 15 of a form as described above is located in the open end of housing portion 12, where it is retained by a grill 16. This open end may have a protective cover 17 releasably connected thereto in a spaced disposition above and around the end to define an air inlet channel as indicated by arrows. The remaining housing portion 13 is elongated and surrounds, as a protective cover, a bag filter 18 suspended therein with its mouth uppermost to receive air blown by the fan. Portion 13 is suitably releasable to facilitate insertion and removal of the bag filter.

The instrument is intended to be used generally upright as illustrated with the lower open end of the portion 13 clear of the ground or other obstructions. This can be effected in any suitable manner at a fixed site. Alternatively, the instrument can be suspended in front of a worker by use of straps passing around his neck and waist.

The fan is suitably of axial form, which is likely to be simpler than an alternative form such as a centrifugal fan.

FIG. 3 schematically illustrates yet another form of gravimetric particle sampling instrument which in this case is specifically intended for personal use by incorporation in a helmet. The helmet in fact accords with the afore-mentioned Patents and requires no detailed description thereover other than to note that the present invention provides in the helmet a pre-filter 20, battery-operable axial fan 21, and a bag filter 22, these items being located in a passageway leading through the helmet from its rear, between the helmet outer shell 23 and inner shell or harness 24, and then forwardly and downwardly behind a visor 25 to atmosphere, the filtered air serving for respiration by the user.

FIG. 4 schematically illustrates a pre-filter constituted by multiple contiguous layers of foam material having differing characteristics such as described above.

Figure 5A:
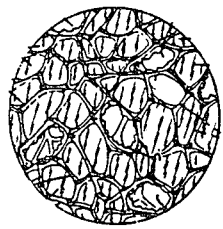
Figure 5B:
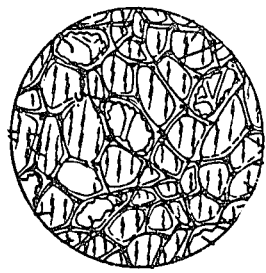
Figure 5C:
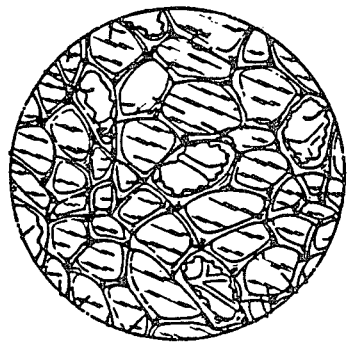
Figure 5D:
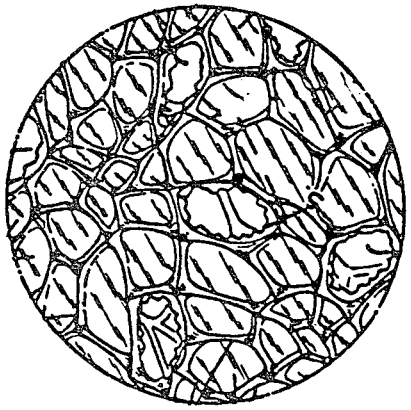
Figure 5E:
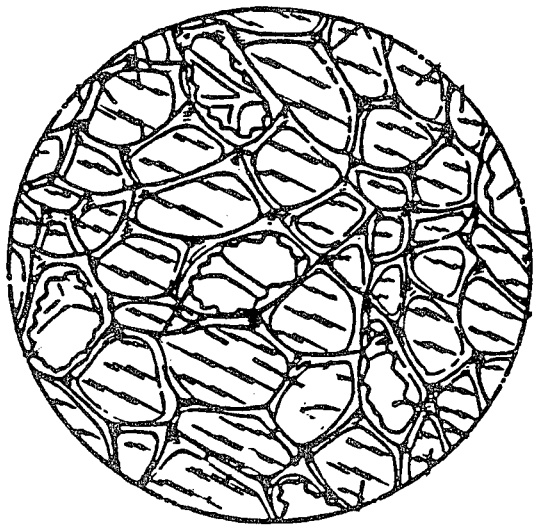

FIGS. 5A-E illustrate schematically the filter network for each of the layers of FIG. 4 in greatly enlarged detail with FIG. 5A illustrating layer A of FIG. 4, FIG. 5B illustrating layer B of FIG. 4, FIG. 5C illustrating layer C of FIG. 4, FIG. 5D illustrating layer D of FIG. 4 and FIG. 5E illustrating layer E of FIG. 4.

While reference has been made to the use of a bag form for the main, respirable particle filter, alternative forms can be used involving flat, pleated or other structures.

We claim:

1. A respirable particle sampling instrument comprising a housing defining an air passageway therethrough, an electric fan mounted in said passageway to draw and pass air into and through said passageway, a main filter located across said passageway to collect respirable particles borne by said air passing therethrough, and a pre-filter located across said passageway upstream of said main filter to collect non-respirable particles borne by said air passing therethrough, said pre-filter being formed by a random fibrous network having interstices of such size and distribution as to capture a major proportion of the non-respirable airborne particles in an air flow therethrough within a prescribed range of velocity for which particle capture is predominantly by intertial impaction.

2. An instrument according to claim 1 wherein said network is formed by a porous foamed plastics material.

3. An instrument according to claim 2 wherein said network is formed by a structure of contiguous layers of said material having successively changed pore sizes and distribution therethrough.

4. An instrument according to claim 2 wherein said material is a polyester.

5. An instrument according to claim 2 wherein said material has an oil coating.

6. An instrument according to claim 1 wherein said housing is in the form of a helmet.

7. An instrument according to claim 1 wherein said main filter is a bag form located downstream of said fan, and said pre-filter is located upstream of said fan.

* * * * *